(12) United States Patent
Walker et al.

(10) Patent No.: US 7,929,745 B2
(45) Date of Patent: *Apr. 19, 2011

(54) METHOD AND SYSTEM FOR CHARACTERIZATION OF KNEE JOINT MORPHOLOGY

(75) Inventors: Kevin Walker, Sheffield (GB); Jane Haslam, Bucks (GB); Anthony Holmes, Cheshire (GB)

(73) Assignee: Optasia Medical Limited, Cheadle (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/761,693

(22) Filed: Apr. 16, 2010

(65) Prior Publication Data

US 2010/0272332 A1 Oct. 28, 2010

Related U.S. Application Data

(63) Continuation of application No. 11/376,868, filed on Mar. 16, 2006, now Pat. No. 7,760,923.

(60) Provisional application No. 60/664,912, filed on Mar. 24, 2005.

(51) Int. Cl.
G06K 9/00 (2006.01)
A61B 8/00 (2006.01)
(52) U.S. Cl. ........................................ 382/128; 600/427
(58) Field of Classification Search .......... 382/128–133, 382/203, 209, 217, 254, 266, 161, 165, 194; 600/427, 407; 128/898, 920, 922–923; 345/629–634, 641; 435/4, 39, 288.7; 703/11
See application file for complete search history.

(56) References Cited

U.S. PATENT DOCUMENTS

| | | | | | |
|---|---|---|---|---|---|
| 5,360,446 | A | * | 11/1994 | Kennedy | 128/898 |
| 5,871,018 | A | * | 2/1999 | Delp et al. | 128/898 |
| 6,002,859 | A | * | 12/1999 | DiGioia et al. | 703/11 |
| 6,190,320 | B1 | * | 2/2001 | Lelong | 600/439 |
| 6,701,174 | B1 | * | 3/2004 | Krause et al. | 600/407 |
| 6,711,432 | B1 | * | 3/2004 | Weiss et al. | 600/427 |
| 6,963,825 | B1 | * | 11/2005 | Morikawa et al. | 703/2 |
| 7,027,650 | B2 | | 4/2006 | Williame et al. | |
| 7,227,981 | B1 | * | 6/2007 | Fleute et al. | 382/132 |

(Continued)

FOREIGN PATENT DOCUMENTS

EP 1349098 10/2003

(Continued)

OTHER PUBLICATIONS

Rhodri H. Davies, Carole J. Twining, Timothy F. Cootes, John C. Waterton, Christopher J. Taylor: A minimum description length approach to statistical shape modeling. IEEE Trans. Med. Imaging 21(5): 525-537 (2002).*

(Continued)

*Primary Examiner* — Vu Le
*Assistant Examiner* — Andrae S Allison
(74) *Attorney, Agent, or Firm* — Wilmer Cutler Pickering Hale and Dorr LLP

(57) ABSTRACT

A method and system for characterizing a knee joint in terms of its skeletal morphology. A plurality of loci associated with a model of skeletal structure of a knee joint are fitted and used to parameterize positions of the plurality of loci in a given subject and, thereby, to derive parameters of a deformable statistical template. The skeletal morphology is then characterized on the basis of the derived parameters of the deformable statistical template.

27 Claims, 3 Drawing Sheets

U.S. PATENT DOCUMENTS

| | | | |
|---|---|---|---|
| 7,388,972 B2 * | 6/2008 | Kitson | 382/128 |
| 2003/0053673 A1 | 3/2003 | Dewaele | |
| 2003/0210813 A1 | 11/2003 | Oosawa | |
| 2008/0031412 A1 | 2/2008 | Lang et al. | |
| 2008/0118137 A1 | 5/2008 | Chen et al. | |

FOREIGN PATENT DOCUMENTS

| | | | |
|---|---|---|---|
| EP | 1424650 | * | 6/2004 |
| EP | 1598778 | | 11/2005 |
| GB | 2402470 | | 12/2004 |
| WO | WO-2006/104707 | | 10/2006 |
| WO | WO-2008/087556 | | 7/2008 |
| WO | WO-2009/154977 | | 12/2009 |

OTHER PUBLICATIONS

Duryea J, Li J, Peterfy CG, Gordon C, Genant HK. Trainable rule-based algorithm for the measurement of joint space width in digital radiographic images of the knee. Med Phys. 2000; 27(3):580-591.*

T.F. Cootes and C.J. Taylor, "Anatomical statistical models and their role in feature extraction", British Journal of Radiology, 2004, vol. 77, pp. S133-S139.*

Markus Fleute, Stephane Lavallee, Remi Julliard, Incorporating a statistically based shape model into a system for computer-assisted anterior cruciate ligament surgery, Medical Image Analysis, vol. 3, Issue 3, Sep. 1999, pp. 209-222.*

Fleute, M. and Lavallée, S. 1999. Nonrigid 3-D/2-D Registration of Images Using Statistical Models. In Proceedings of the Second international Conference on Medical Image Computing and Computer-Assisted intervention (Sep. 19-22, 1999).*

Bland and Aaltman *British Medical Journal*, 1996; 313:744.

Boini et al., *Annals of the Rheumatic Diseases*, 2001; 60: 817-827.

Brett, A.D. "Statistical Modeling for the Assessment of Vertebral Shape in vivo" Optasia Medical Power Point Presentation, BioImaging Seminar, May 31, 2007 (7 pages).

Brett, A.D. et al. "Automated Assessment of Vertebral Shape by Statistical Shape Modelling on Lateral radiographs" ABSMR Abstract Publication. Sep. 14, 2007 (2 pages).

Brett, A.D. et al. "Automated Assessment of Vertebral Shape on Lateral Radiographs by Statistical Shape Modeling" RSNA 2007 Abstract, Nov. 25, 2007 (1 page).

Brett, A.D. et al. "Automated Assessment of Vertebral Shape by Statistical Shape Modeling on Lateral Radiographs" ASBMR Poster Presentation, Sep. 19, 2007 (1 page).

Bruynesteyn et al., *Arthritis & Rheum*, 2002; 46(4): 913-920.

Cootes T.F. et al., "Active Appearance Models", European Conference on Comptuer Vision, vol. 2, No. 1, Jan. 1, 1998, pp. 484-498.

Cootes T.F. et al., "Use of Active Shape Models for Locating Structures in Medical Images", Image and Vision Computing, vol. 12, No. 6, Jul. 1, 1994, pp. 355-365.

Cootes T.F., et al., "Constrained Active Appearance Models", Proceedings of the Eight IEEE International Conference on Computer Vision, Jul. 7-14, 2001, vol. 1, pp. 748-754.

Cootes, et al., *Training Models of Shape from Sets of Examples*, in Proc. BMVC Springer-Verlag, pp. 9-18, 1992.

Cootes, T.F. and Taylor, C.J. "Anatomical statistical models and their role in features extraction," *Brit. J. Radiol.* 77(2004):S133-S139.

Davies, R.H. et al. "A minimum description length approach to statistical shape modeling," *IEEE Trans. Med. Imag.* 21(5) May 2002: 525-537.

Duryea, J. et al. "Trainable rule-based alforithm for the measurement of joint space width in digital radiographic images of the knee," *Med. Phys.* 27(3) (Mar. 2000):580-591.

European Examination Report, European Patent Application No. 06 738 603.7, dated Jul. 24, 2008 (7 pages).

Fleute, M. "Nonrigid 3-D/2-D registration of images using statistical models," Lecture Notes in Computer Science, Springer Verlag, New York, NY. US (Sep. 19, 1999):138-147.

Fleute, M. et al. "Incorporating a statistically based shape model into a system for computer-assisted anterior cruciate ligament surgery," *Med. Imag. Anal.* 3(3):209-222 (1999).

Genant et al., *Arthritis Rheum*, 1998; 41: pp. 1583-1590.

International Search Report and Written Opinion of the International Searching Authority, the European Patent Office, for International Application No. PCT/IB2008/000574, dated Jul. 30, 2008, 12 pages.

International Search Report and Written Opinion of the International Searching Authority, the European Patent Office, for International Application No. PCT/US2006/009565, dated Sep. 4, 2006, 10 pages.

International Search Report of the International Searching Authority, the United States Patent and Trademark Office, for International Application No. PCT/US2009/045276, dated Jul. 20, 2009, 1 page.

Johnson and Wichern, *Applied Multivariate Statistical Analysis*, pp. 458-513 (5th Edition, 2002).

Kainberger F. et al., "Computer Assisted Radiologic Diagnostics of Arthritic Joint Alterations", Zeischrift Fur Rheumatologies, vol. 65, No. 8, Dec. 1, 2006, pp. 676-680.

Langs et al., "Model-Based Erosion Spotting and Visualization in Rheumatoid Arthritis" Academic Radiology, vol. 14, No. 10, Sep. 20, 2007, pp. 1179-1188.

Langs et al., *Scandinavian Conference on Image Analysis 2003, Lecture Notes in Computer Science* 2749, pp. 454-461, 2003 and *Academic Radiology* 2007.

Patent Cooperation Treaty International Search Report, dated Jul. 30, 2008, 5 pages.

Peloschek et al., "Quantative Imaging in Rheumtoid Arthritis: From Scoring to Measurement", Der Radiologe; Zeitschrift Fur Diagnostische Und Interventionelle Radiologies, Radioonkologie, Nuklearmedizin, vol. 46, No. 5, May 1, 2006, pp. 411-416.

Rau et al., *The Journal of Rheumatology*, 1995; 22: pp. 1976-1982.

S.J. Caulkin, *Generating Synthetic Abnormalities in Digital Mammograms Using Statistical Models*, Ph.D. Thesis, University of Manchester, 2001.

Scott et al., *British Journal of Rheumatology*, 1995; pp. 34-56.

T.F. Cootes and C.J. Taylor, *Statistical Models of Appearance for Medical Image Analysis and Computer Vision*, in Proc. SPIE Medical Imaging, 2001.

Van Der Heijde et al., *Rheumatology*, 1999; 38: 1213-20.

Van Der Heijde et al., *The Lancet*, 1989; i: pp. 1036-1038.

Zhang et al., *Local Features and Kernels for Classification of Texture and Object Categories: A Comprehensive Study*, International Journal of Computer Vision, Sep. 2006.

* cited by examiner

METHOD AND SYSTEM FOR CHARACTERIZATION OF KNEE JOINT MORPHOLOGY

CROSS-REFERENCE TO RELATED APPLICATIONS

This application is a continuation of prior U.S. patent application Ser. No. 11/376,868, now U.S. Pat. No. 7,760,923, filed on Mar. 16, 2006, entitled Method and System For Characterization of Knee Joint Morphology, which claims the benefit under 35 U.S.C. §119(e) of U.S. Provisional Patent Application No. 60/664,912, filed Mar. 24, 2005, entitled Method and System For Characterization of Knee Joint Morphology, both of which are incorporated herein by reference.

BACKGROUND OF THE INVENTION

1. Field of the Invention

The invention relates generally to the characterization of the morphology of knee joints, each knee joint at one or more times, for purposes of research or for diagnosis of pathologies in a particular individual.

2. Description of Related Art

Studies of the anatomy of the knee require quantitative characterization of structural parameters. As one particular example, anatomical studies of knees in identified populations require a measure of knee osteoarthritis (OA), a slow progressive disease characterized by loss of cartilage in the joint and leads to loss of joint movement and increased pain. Of the two primary compartments (lateral and medial) of the knee, OA is seen mainly in the medial compartment, due to the higher weight-bearing load borne here. Longitudinal evaluation of the disease in an individual relies on clinical and radiographic features, chiefly pain, disability and structural changes. Disease-modifying therapies are currently under development and these will rely upon the accurate and precise assessment of the progression of the disease.

In current practice, the primary endpoint used in population studies, clinical trials, and epidemiological studies of OA of the knee, is the surrogate measure of radiographic minimum Joint Space Width (mJSW), measured between either of the weight-bearing surfaces of the femoral condyles and the tibial plateau from a radiograph taken in a semi-flexed position, as shown in the radiograph of FIG. 1. The progressive loss of cartilage is measured by narrowing of the mJSW. Since OA is seen mainly in the medial compartment, the mJSW is usually measured in this compartment only.

The measurement of mJSW is usually made by a trained physician using a graduated hand-held lens while reviewing the radiograph on a light-box. Using this method, it is difficult to avoid significant inter- and intra-observer variation due to the subjectivity of the human observer. Moreover, since the mJSW is usually only measured in the medial compartment, it is possible that OA in the lateral compartment will elude detection, and indeed, some patients have primary lateral compartment disease. Finally, in that the mJSW is a single measure of disease progression, effects in the whole joint may be masked by reliance on a single indicator.

In order to address the major problem of human subjectivity, computer analysis of digitized knee radiographs for the measurement of mJSW has been employed by several authors. One method of computer analysis for deriving mJSW from X-ray images was described by Duryea et al., 27 *Med. Phys.*, pp. 580-91 (March, 2000), herein incorporated by reference. Moreover, surrogate outcome measures for characterizing the knee joint space other than the mJSW, have been studied and compared with mJSW, for example, by Duryea et al., 11 *Osteoarthritis & Cartilage*, pp. 102-110 (2003), which is incorporated herein by reference. The foregoing methods are examples of feature-based analytical techniques.

It is desirable, however, to supplement radiographic mJSW measurement with a technique that contributes to greater sensitivity to OA in quantitative measures than is available using non model-based approaches, particularly with a view to clinical evaluation of potential therapies that may be performed more quickly with fewer patients by virtue of the enhanced sensitivity.

BRIEF SUMMARY OF THE INVENTION

In accordance with preferred embodiments of the present invention, a method is provided for characterizing a knee joint in terms of a model parameterization. The method has steps of:

a. creating a deformable statistical template characterized by a set of parameters that, as a set, span an abstract vector space representing the set of spatial positions of specified features of the knee joint, each vector uniquely describing its variation from a population mean;

b. fitting, at runtime, in a two-dimensional image of the skeleture of a knee, a plurality of loci associated with the specified features to allow parameterization in terms of a deformable statistical template;

c. parameterizing positions of the plurality of loci in a given subject to derive values for parameters of the deformable statistical template; and d. characterizing the skeletal morphology of the knee of the given subject on the basis of either a subset of the plurality of loci, and/or the derived parameters of the deformable statistical template.

It is to be understood that where the term "subset" is used in the description of the present invention or in any appended claim, in connection with elements comprising a set, the term "subset" is to be understood as encompassing either a proper, or a full, subset of the entirety of the set of elements. Furthermore, the term "locus" is used to mean one of the plurality of points within some "distance" of a point (in the vector space) that define a feature. "Distance" refers, generally, to a norm defined over the vector space.

In accordance with other embodiments of the invention, the two-dimensional image may be a radiograph obtained by transmission of penetrating radiation through the knee joint, such as by transmission of x-rays through the knee joint. The method may further include predicting a clinical outcome of a therapeutic modality based on characterization of the skeletal morphology in terms of parameters of the deformable statistical template.

In accordance with further embodiments of the invention, the step of creating a deformable statistical template may include defining the set of parameters on the basis of statistical analysis of a set of two-dimensional images of knees, while the step of fitting, at runtime, a plurality of loci associated with specified model features may include receiving operator input. Steps (c) and (d) of the method recited above may be repeated at successive points in time for describing evolution of the skeletal morphology over time.

In accordance with yet further embodiments of the invention, an additional step may include performing a clinical intervention between successive iterations of step (c). The step of parameterizing positions may include successive approximation of positions of the plurality of loci. The step of characterizing the skeletal morphology of the knee may include estimating the joint separation width at a specified position in the medial or lateral compartment, or estimating the minimum joint separation in at least one of the medial and lateral compartment.

A further aspect of the invention provides a method for characterizing a knee joint in terms of its skeletal morphology. This method has steps of:

a. fitting, at runtime, in a two-dimensional image of the skeleture of a knee, a plurality of loci associated with specified features to allow parameterization of a deformable statistical template;

b. parameterizing positions of the plurality of loci in a given subject to derive parameters of the deformable statistical template; and c. characterizing the skeletal morphology on the basis of either a subset of the plurality of loci, and/or the derived parameters of the deformable statistical template.

Finally, in accordance with the invention, a computer program product may be provided for use on a computer system for characterizing the skeletal morphology of a knee joint of a subject. The computer program product has program code for storing loci associated with specified skeletal features in a two-dimensional image of a knee joint into a computer memory, program code for parameterizing positions of the plurality of loci in a given subject to derive parameters of a deformable statistical template, and program code for characterizing the skeletal morphology on the basis of either a subset of the plurality of loci, and/or the derived parameters of the deformable statistical template.

BRIEF DESCRIPTION OF THE SEVERAL VIEWS OF THE DRAWINGS

The foregoing features of the invention will be more readily understood by reference to the following detailed description, taken with reference to the accompanying drawings, in which.

DETAILED DESCRIPTION

In accordance with preferred embodiments of the current invention, a computer analysis of a digitized knee radiograph is carried out either automatically or semi-automatically using a deformable statistical template that has been produced, for example, by the statistical analysis of a number of hand-annotated example radiographs of the knee.

The invention described herein and claimed in any appended claims is applied to data obtained by imaging of a knee joint, of a person or animal, by the use of penetrating electromagnetic radiation such as x-rays, for example. Typically, two-dimensional radiographs representing the transmission of penetrating radiation through the joint are employed. While it is to be understood that the invention is not limited in scope to a particular modality of imaging nor to a particular modality for storing and manipulating the image, or images, obtained, there are advantages that arise from particular modalities, such as the high spatial resolution advantageously provided by high energy (x-ray or gamma ray) radiation.

Analysis of the image of the knee joint (referred to, herein, without limitation, as a 'radiograph') proceeds, as described below, on the basis of a 'model' which is applied to the input data. As used herein and in any appended claims, the term 'model,' generally, refers to any mathematical description that provides for parameterization of the position and/or motion of a subject or its component parts. The application of the methods described herein to any model of knee image data is within the scope of the present invention as claimed. When a model is referred to herein as "statistical," it is to be understood as based on an analysis of variation of parameters among members of a population of subjects.

Figure 1:
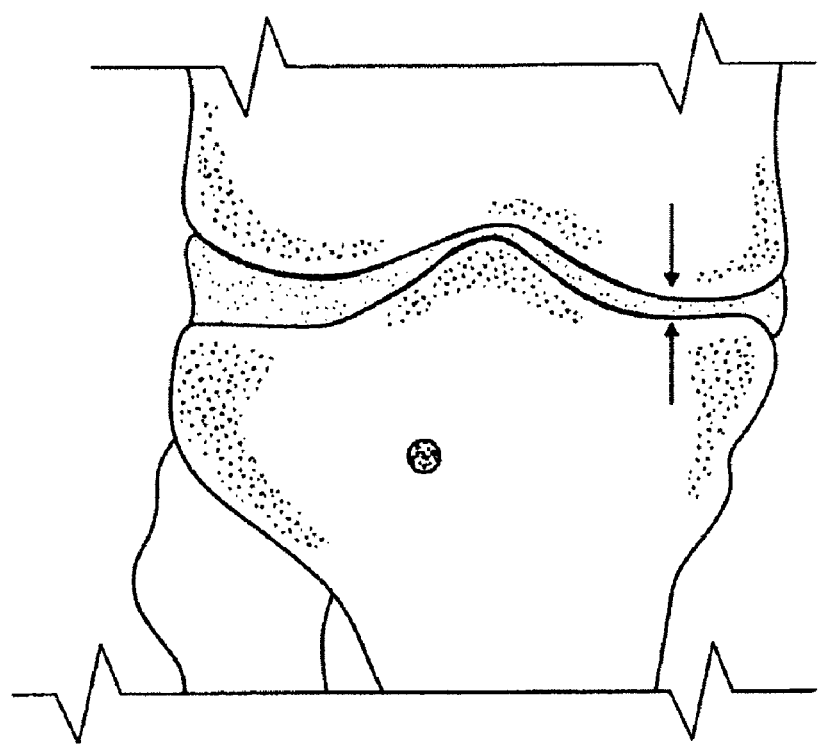
FIG. 1 depicts the prior art standard measurement of the mJSW in the medial compartment as surrogate measure of knee osteoarthritis.
Figure 2:
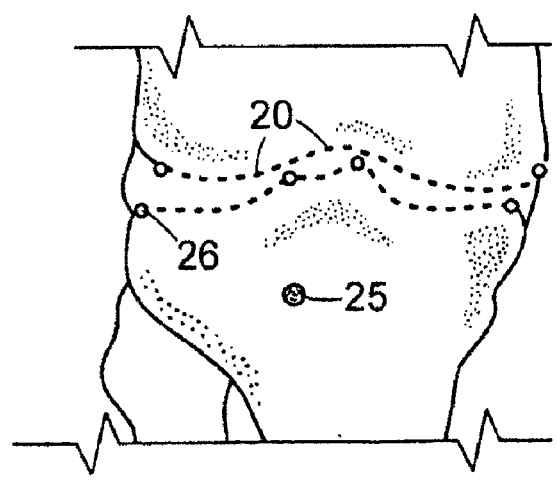
FIG. 2 depicts a typical set of anatomical landmarks defined for application of the invention.

More particularly, the invention will be described with reference to a class of models wherein the model represents the average relative positions of a specified set of 2D point positions on the knee, along with a mathematical description of the way these relative positions vary in normal circumstances among individuals or in a particular individual with the passage of time or due to an intervening circumstance, such, for example, as the progression of a disease. Practice of the present invention is posited upon the existence of a mathematical model of 'plausible' morphologies, wherein morphology encompasses shapes and shape variation, and may also encompass other aspects of appearance such as the texture of a modeled object. A method, described below, is employed for applying the model to data obtained from an image of an actual knee. The method is not, however, specific to any particular placement of the point set, and is illustrated in FIG. 2, purely by way of example, and without limitation, as a set of points (or 'landmarks') 20 placed automatically, or semi-automatically, on the tibial spines, peripheral boundaries of the joint, margins of the femoral condyles and tibial plateau. A ball-bearing 25, used as a calibration target of known diameter, to allow measurements to be expressed in standard units of length, may also be found in the image shown in FIG. 2.

During run-time application of embodiments of the present invention, the specified points are preliminarily identified (a process referred to, herein, as segmentation), in an image of a knee joint, by a program element trained to identify these positions. In semi-automatic analysis, the user of the application is asked to define some subset (proper or full) of the landmarks on the knee radiograph (larger dots 26 in FIG. 2) that were identified, either automatically or semi-automatically, in creation of the deformable statistical template. These positions are defined in such a manner as to effectively 'describe' the radiographic appearance of the knee—whether by relation to extremal features or otherwise.

Even though the precise morphology of the knee joint varies among subjects and changes with time, these landmarks remain identifiable, for the most part. The template is statistical in that it models the distribution (with the mean and 'normal' variation, or other moments serving, without limitation, as representative characterizations) of the radiographic appearance (as discussed above) of the knee across an ensemble of subjects. The template, thus, allows for parameterization of the morphology in terms of a finite number of values, with the present invention independent of any particular scheme of parameterization.

A mathematical model of the plausible positions of points may be built, for application in the present invention, as now described. A set of training 2D data blocks, are taken from an ensemble of radiographic images of knees. These data may be augmented by manual adjustment prior to the process of model building.

For the purpose of building a model, the relative positions of the 2D points are consequential rather than their 'absolute' space-referenced positions. Thus, in building the model, the first step is typically to align each frame of 2D data to a common reference frame, as may be achieved by using one of various standard alignment techniques, such as by 'Procrustes Analysis', which is described by Horn, *Closed Form Solution of Absolute Orientation Using Unit Quaternions*, J. Optical Society, vol. A 4, pp. 629-42 (April, 1987), which is incorporated herein by reference.

The model provides for a compact mathematical description of the variation in relative 2D point positions among frames of the training data. Once the data are aligned, this can be done by one or more of several types of statistical modeling techniques, including, for example, 'Principal Component Analysis' as described by Johnson and Wichern, in *Applied Multivariate Statistical Analysis*, pp. 458-513 (5$^{th}$ Edition, 2002).

In one set of embodiments, the model may consist of an 'average' shape for the 2D data along with a set of mathematical functions which describe how the shapes can change. By feeding a vector of control numbers or 'model parameters' into the mathematical functions any plausible set of 2D point coordinates can be generated. While the model parameters may span a space of model shape excursions, such is not necessarily the case for practice of the invention as claimed. Moreover, the model may be linear, in the sense in which motions correspond to linear combinations of points moving along straight lines (rather than, for example, arcs or curves). However, the invention is not limited in its applicability to such models.

Figure 3:
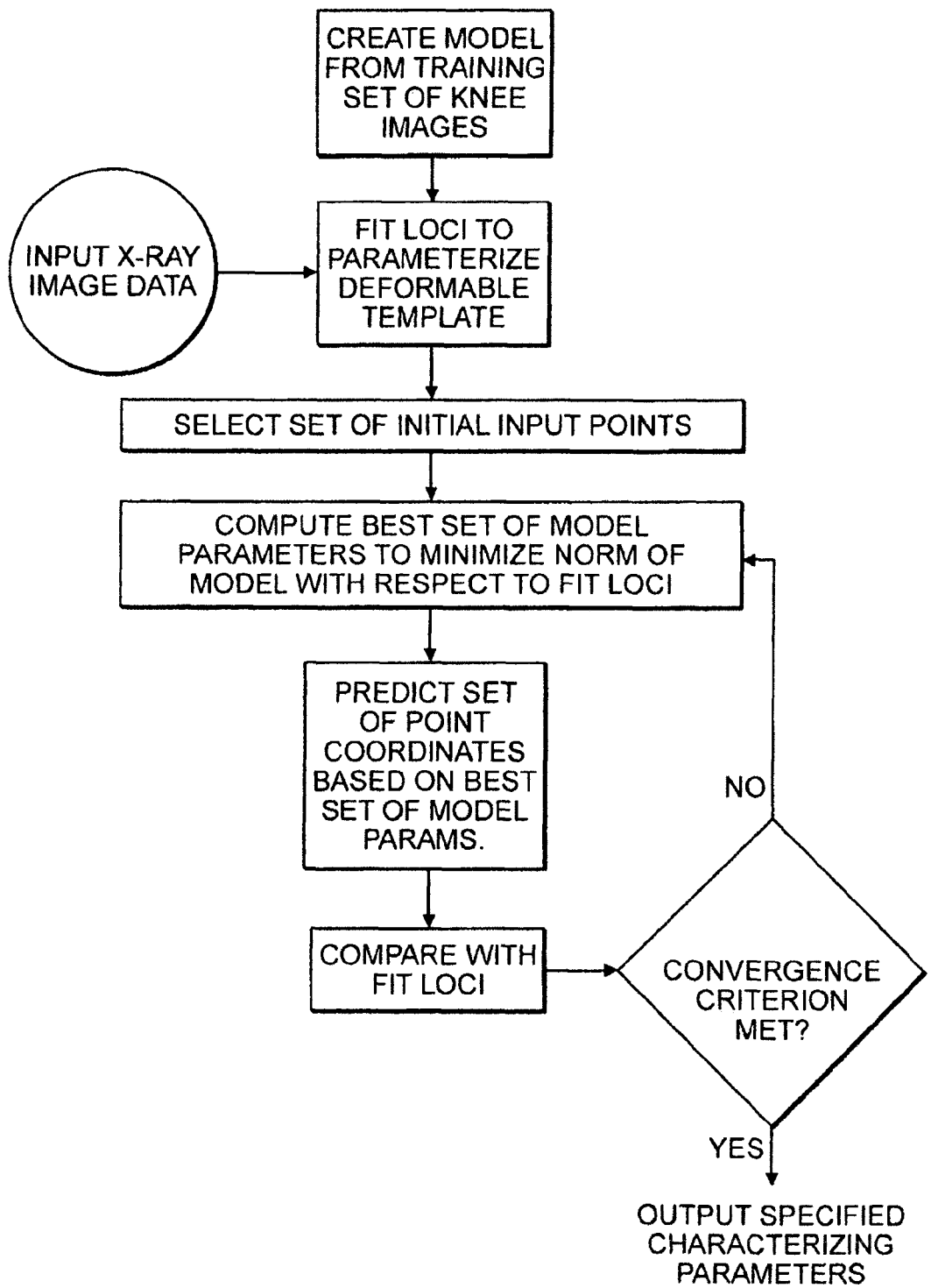
FIG. 3 is a flow chart depicting an application of preferred embodiments of the invention to image data of a knee.

As will now be discussed with reference to the flow diagram of FIG. 3, embodiments of the present invention use the model, once trained as heretofore described, to segment the image, i.e., to locate the 2D point coordinates that characterize the skeletal morphology of the knee. In accordance with preferred embodiments of the invention, a number of sets of putative input point locations are generated, such as randomly or across a set of predefined possible locations, for example. Each of these sets is tested in order to identify a suitable set of initial input point locations based upon their positioning within 'distances' of neighboring points that the model recognizes as 'reasonable.' The term 'distance', as used herein and in any appended claims refers to a norm with respect to the parameterized variables of the model, and may correspond to a Euclidean norm, but need not, within the scope of the invention. Once initial input 2D point locations have been identified, the best set of alignment parameters is found, to match these locations with the locations of corresponding points in the model, i.e., to transform all coordinates to the reference frame of the model, in such a way as to maximize the probability that the model parameters describe the actual image. Iterations, as described below, are then employed for localized fitting. An algorithm for performing such a segmentation step is described in T. F. Cootes and C. J. Taylor, *Statistical Models of Appearance for Medical Image Analysis and Computer Vision*, in *Proc. SPIE Medical Imaging*, (2001), appended hereto and incorporated herein by reference.

An initial set of points can be described as a vector X, $$X=\{x_1, x_2 \ldots x_n, y_1, y_2 \ldots y_n\},$$

where $(x_i, y_i)$ are the 2D coordinates of the point with index i.

The points when aligned to the reference frame of the model using, e.g., Horn (supra) are described as a vector X' where X' is the result of applying the computed alignment transformation, T, to X, $$X'=T(X),$$

where T is the matrix of computed transformation parameters.

The model is some function, F, which generates a vector of parameters, b, given a set of input point coordinates $$b=F(X')$$

In one set of embodiments, where the model consists of an 'average' shape for the 2D data along with a set of mathematical functions which describe how the shapes can change, b is calculated using:

$$b=A(X'-X'_m)$$

where $X_m$ is the vector of 2D point coordinates for the 'average' shape and A is a matrix learned during the training phase using, for example, Principal Components Analysis, as described in 'Principal Component Analysis' as described by Johnson and Wichern, in *Applied Multivariate Statistical Analysis*, pp. 458-513 (5$^{th}$ Edition, 2002) which is incorporated herein by reference.

To estimate a set of point coordinates given a set of model parameters the 'inverse', (which, in most cases, can only be an approximate inverse) of F, F' is used $$X_e'=F'(b)$$

where $X_e$ is the estimated value of the 2D coordinates for a given set of parameters, b. If the model is built using Principal Components Analysis then this is written as:

$$X_e=X_m+A'(b)$$

where A' is the pseudoinverse of A which in the case of Principal Component Analysis is identical to the transpose of A.

Various model-fitting algorithms may be used to accomplish the foregoing step. In one embodiment, a simple, unweighted least squares estimate of the model values is computed:

$$b=A(X'-X_m')$$

These values are used predict the values of the entire 2D point vector in the model frame of reference according to:

$$X_e'=F'(b)$$

T', the inverse of the transformation matrix T, is used to estimate the entire 2D point vector in the original frame of reference:

$$X_e=T'(X_e').$$

This subsequent set of points is now realigned with the model frame of reference and the process that has been described is repeated. A best set of alignment parameters is found and then the fitting algorithm is applied to derive a best set of model parameters. The best set of model parameters is then used to generate another set of points.

This iterative process is repeated until there is convergence (within a specified criterion) or else until a specified maximum number of iterations have been executed. When the iterations have finished, the output of the final step is a solution for the full set of 2D points as fit by the model parameters.

A final segmentation (i.e., identification, in the radiograph, of the specified initialization points) may now be used to extract a number of measurements from the radiograph, such as those are outlined below, which are presented as examples only and not as a comprehensive set:

The mJSW in either the lateral or medial compartment.

The JSW at any position in the medial or lateral compartment, the position of the JSW measurement may be parameterized along a line from the tibial spine to a specified position at an edge of the joint, thus this measurement may be compared at various time points in a longitudinal study.

A defined measure, having the dimensions of an area, characterizing a specified region subtended by either compartment.

Since a deformable statistical template has been used to detect and annotate the joint, a parameterization of the joint shape may be determined from optimized fit of this template. Therefore, the 'shape', in an abstract sense, of the joint may be compared to that of a 'universe' of 'normal' joints, or else the changes in shape parameters at time points in a longitudinal study may be used as a novel measurement of disease progression. Changes may be mapped in specified measures over the course of a period of time, whether in the presence of a medical intervention, or otherwise. The case of a medical intervention, in the most general sense, will be referred to herein, and in any appended claims, as a "therapeutic modality," and will include the administration of medicinal agents, but will not be limited thereto.

Figure 4:
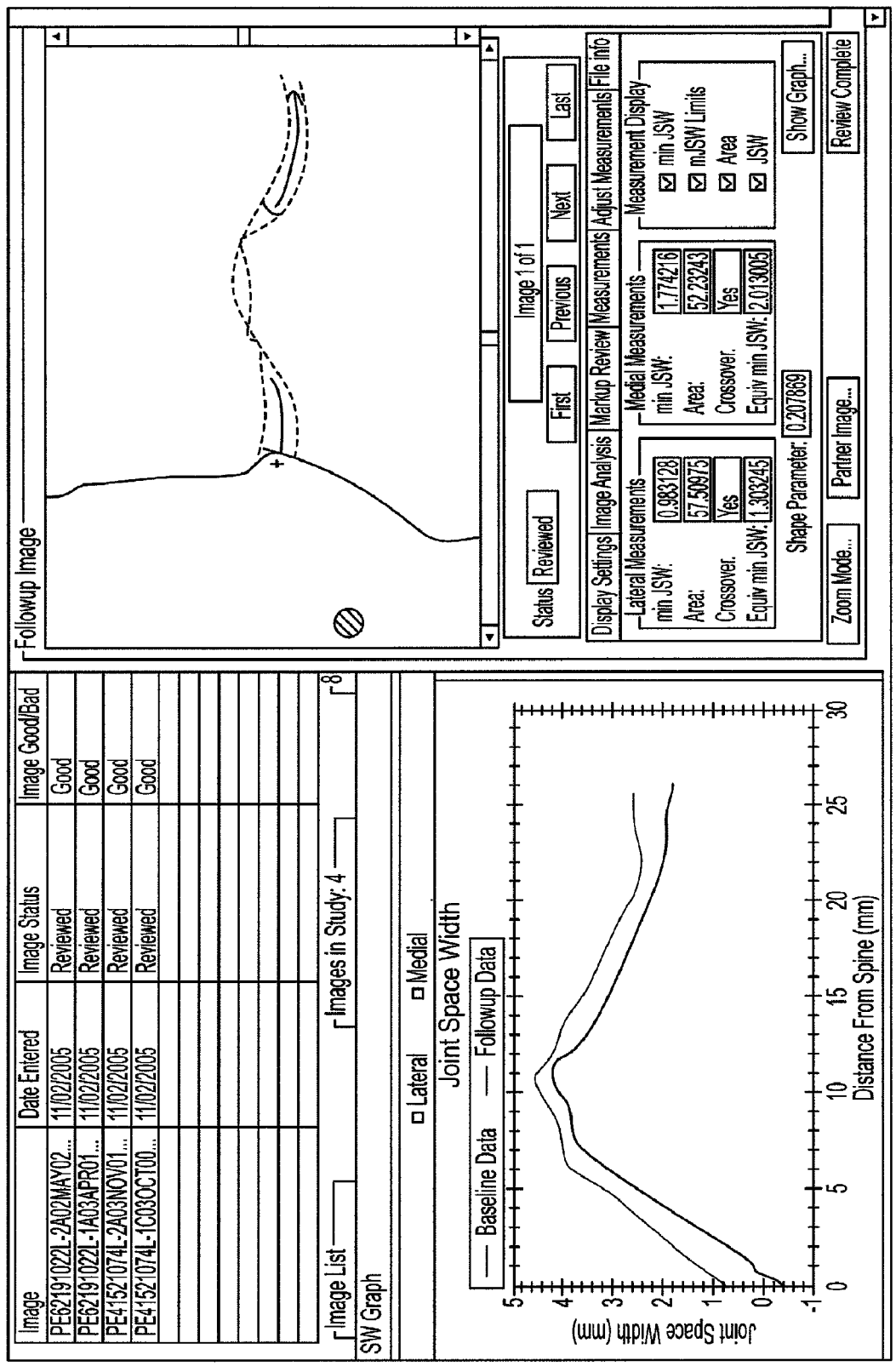
FIG. 4 depicts software analysis of specified measures of knee joint morphology, in accordance with preferred embodiments of the present invention.

A screenshot of a software application demonstrating several of these measurements being performed is shown in FIG. 4. In particular, the following measures are examples of measures that may be employed, in accordance with the invention, for characterization of knee morphology:

Cartilage Area Measurement

For both baseline and follow-up images, and for either compartment, an area is measured, defined by the tibial plateau, the femoral condyle and the joint space widths (JSWs) at either end of the compartment.

Joint Space Width (JSW) Profile Measurement

For both baseline and follow-up images, and for either compartment, a profile of Joint Space Width (JSW) may be measured along the entire length of the tibial plateau. The JSW at a given point is the minimum distance between the tibial boundary and the femoral boundary. The JSW profile is measured (in mm) as a function of the distance along the medial axis of the joint from the tibial spine.

Minimum JSW Measurement

For both baseline and follow-up images, a minimum JSW may be measured in both the medial and the lateral compartment. The minimum JSW is the minimum value of the JSW profile measurement in a given range along the tibial plateau. By default, the minimum is found between the inner extent of the cartilage area measurement, and the outer extent of the JSW profile measurement.

Equivalent JSW Measurement

For follow-up images, and for either compartment, the JSW may be measured at the estimated position (along the tibial plateau) at which the mJSW was calculated on the baseline image. This measurement requires that both baseline and follow-up images for a patient are attached to the study.

Cross-Over Flag

The cross-over flag is a flag which indicates whether the boundary of the tibia crosses over the boundary of the femur, for either the medial compartment or the lateral compartment. In these cases where cross-over is found, it may be desirable to ignore the results.

Shape Measure

For a given pair of baseline and follow-up images, the system may calculate a statistic corresponding to how much the overall shape of the knee has changed between the baseline knee and the follow-up knee. The higher the value of this statistic, the more change there is between baseline and follow-up. The units of the Shape Measure are mm, and the figure corresponds to the mean amount by which each point on the segmented knee boundary has moved between the baseline and follow-up knee, measured in the same frame of reference. This measurement requires that both baseline and follow-up images for a patient be attached to the study. This should allow the rapid identification of 'interesting' images that may warrant extended manual investigation.

The disclosed methods for characterizing the morphology of a knee joint may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The described embodiments of the invention are intended to be merely exemplary and numerous variations and modifications will be apparent to those skilled in the art. All such variations and modifications are intended to be within the scope of the present invention as defined in the appended claims.

We claim:

1. A computer-automated method for estimating at least one characteristic of a knee joint based on a model parameterization, the method comprising:
   a. creating a deformable statistical template comprising a set of parameters that, as a set, represent spatial positions of features of the knee joint and variations of the spatial positions from a population mean;
   b. a computer system fitting at runtime, in a two-dimensional image of the skeleture of a target knee, a plurality of loci associated with features of the image of the target knee to allow parameterization of the image of the target knee in terms of the deformable statistical template;

c. the computer system parameterizing positions of the plurality of loci in the image of the target knee to derive values for parameters of the deformable statistical template;

d. the computer system estimating a position of a tibial spine and a position near an edge of the target knee on the image of the target knee based on at least one of a subset of the plurality of loci and the derived parameters of the deformable statistical template; and e. the computer system estimating at least one characteristic of at least one position along a line from the estimated position of the tibial spine to the estimated position near the edge of the target knee on the image of the target knee based on at least one of a subset of the plurality of loci and the derived parameters of the deformable statistical template.

2. A method in accordance with claim 1, wherein the at least one characteristic is an area within a compartment on the two-dimensional image of the skeleture of the target knee.

3. A method in accordance with claim 2, wherein the area within the compartment is bounded by a tibial boundary, a femoral boundary, the at least one position along the line from the estimated position of the tibial spine to the estimated position near the edge of the target knee, and a second position along said line.

4. A method in accordance with claim 3, wherein the at least one position along said line is at the tibial spine on the image of the target knee.

5. A method in accordance with claim 4, wherein the second position along said line is at the estimated position near the edge of the target knee on the image of the target knee.

6. A method in accordance with claim 1, wherein the two-dimensional image is a radiograph obtained by transmission of penetrating radiation through the knee joint.

7. A method in accordance with claim 1, wherein the two-dimensional image is a radiograph obtained by transmission of x-rays through the knee joint.

8. A method in accordance with claim 1, further including predicting a clinical outcome of a therapeutic modality based on the determination of the at least one characteristic.

9. A method in accordance with claim 1, wherein the step of creating a deformable statistical template includes defining the set of parameters on the basis of statistical analysis of a set of two-dimensional images of knees.

10. A method in accordance with claim 1, wherein the step of fitting, at runtime, a plurality of loci associated with features of the image of the target knee includes receiving operator input.

11. A method in accordance with claim 1, further comprising repetition of steps (c), (d), and (e) for at least one successive image of the target knee provided at least one successive point in time for describing evolution of the at least one characteristic at the same at least one position along the line from the tibial spine to the position near the edge of the target knee over time.

12. A method in accordance with claim 11, further comprising a step of performing a clinical intervention between successive iterations of step (c).

13. A method in accordance with claim 1, wherein the step of fitting includes successive approximation of positions of the plurality of loci.

14. A method in accordance with claim 1, further comprising displaying the results of the at least one characteristic estimation on a display device.

15. A computer-automated method for estimating at least one characteristic of a knee joint, the method comprising:

a. a computer system fitting, at runtime, in a two-dimensional image of the skeleture of a target knee, a plurality of loci associated with features of the image of the target knee to allow parameterization of the image of the target knee in terms of a deformable statistical template;

b. the computer system parameterizing positions of the plurality of loci in the image of the target knee to derive parameters of the deformable statistical template;

c. the computer system estimating a position of a tibial spine and a position near an edge of the target knee on the image of the target knee based on at least one of a subset of the plurality of loci and the derived parameters of the deformable statistical template; and d. the computer system estimating at least one characteristic of at least one position along a line from the tibial spine to the position near the edge of the target knee on the image of the target knee based on at least one of a subset of the plurality of loci and the derived parameters of the deformable statistical template.

16. A method in accordance with claim 15, wherein the at least one characteristic is an area within a compartment on the two-dimensional image of the skeleture of the target knee.

17. A method in accordance with claim 16, wherein the area within the compartment is bounded by a tibial boundary, a femoral boundary, the at least one position along the line from the estimated position of the tibial spine to the estimated position near the edge of the target knee, and a second position along said line.

18. A method in accordance with claim 17, wherein the at least one position along said line is at the tibial spine on the image of the target knee.

19. A method in accordance with claim 18, wherein the second position along said line is at the estimated position near the edge of the target knee on the image of the target knee.

20. The method of claim 15, further comprising repetition of steps (b), (c), and (d) for at least one successive image of the target knee provided at least one successive point in time for describing evolution of the at least one characteristic at the same at least one position along the line from the tibial spine to the position near the edge of the target knee over time.

21. The method of claim 15, further comprising displaying the results of the at least one characteristic estimation on a display device.

22. A non-transitory computer program product, stored on a computer readable medium, for use on a computer system for estimating at least one characteristic of a knee joint of a subject, the program product comprising:

a. computer program code for storing loci associated with skeletal features in a two-dimensional image of the knee joint of the subject into a computer memory;

b. computer program code for parameterizing positions of the plurality of loci of the image of the knee joint of the subject to derive parameters of a deformable statistical template;

c. computer program code for estimating a position of a tibial spine and a position near an edge of the knee joint of the subject on the image of said knee joint based on at least one of a subset of the loci and the derived parameters of the deformable statistical template;

d. computer program code for estimating at least one characteristic of at least one position along a line from the tibial spine to the position near the edge of the knee joint of the subject based on at least one of a subset of the loci, and the derived parameters of the deformable statistical template.

23. A non-transitory computer program product in accordance with claim 22, wherein the at least one characteristic is an area within a compartment on the two-dimensional image of the skeleture of the target knee.

24. A non-transitory computer program product in accordance with claim 23, wherein the area within the compartment is bounded by a tibial boundary, a femoral boundary, the at least one position along the line from the estimated position of the tibial spine to the estimated position near the edge of the target knee, and a second position along said line.

25. A non-transitory computer program product in accordance with claim 24, wherein the at least one position along said line is at the tibial spine on the image of the target knee.

26. A non-transitory computer program product in accordance with claim 25, wherein the second position along said line is at the estimated position near the edge of the target knee on the image of the target knee.

27. The computer program product of claim 22, further comprising computer program code for comparing at least a first and a second estimated at least one characteristic at the same at least one position, wherein the second estimated at least one characteristic is based on a second image of the knee joint of the subject generated later in time relative to a first image corresponding to the first estimated at least one characteristic.

* * * * *